United States Patent [19]
Bell

[11] 4,307,102
[45] Dec. 22, 1981

[54] PHENANTHRO[2,3-c]PYRAZOLE

[75] Inventor: Malcolm R. Bell, East Greenbush, N.Y.

[73] Assignee: Sterling Drug Inc., New York, N.Y.

[21] Appl. No.: 235,435

[22] Filed: Feb. 19, 1981

[51] Int. Cl.³ .............................................. A61K 31/44
[52] U.S. Cl. .................................... 424/263; 546/271
[58] Field of Search ........................ 546/271; 424/263

[56] References Cited
U.S. PATENT DOCUMENTS
3,842,088 10/1974 Habeck et al. ...................... 546/271

OTHER PUBLICATIONS
Chem. Abstract 84: 69717r.

Primary Examiner—Ethel G. Love
Attorney, Agent, or Firm—Thomas L. Johnson; B. Woodrow Wyatt

[57] ABSTRACT
The compound of the formula

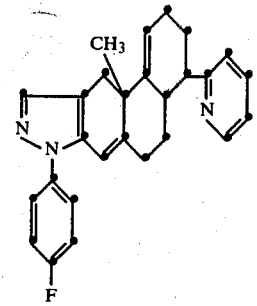

possesses glucocorticoid activity, and is prepared by reacting the compound of the formula

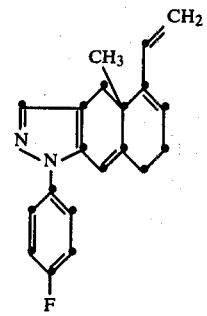

with 2-vinylpyridine.

3 Claims, No Drawings

PHENANTHRO[2,3-C]PYRAZOLE

BACKGROUND OF THE INVENTION (1) Field of the Invention

The present invention relates to a novel polycyclic fused pyrazole compound, its use as an anti-inflammatory agent, and a method of preparation thereof.

(2) Description of the Prior Art

Typical glucocorticoid activity is rarely found in structures which do not possess an intact steroid nucleus. Such activity is found in naturally occurring steroids such as cortisone, hydrocortisone and aldosterone, as well as numerous synthetic modifications thereof, all containing the intact steroid nucleus. An example of a synthetic cortical steroid having high activity is a fluorophenylpyrazole derivative reported by Fried et al., J. Am. Chem. Soc. 85, 236 (1963), having the structure

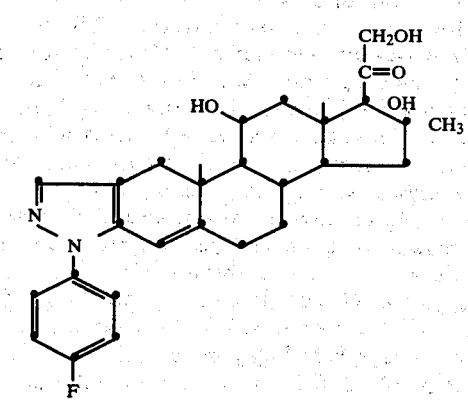

SUMMARY OF THE INVENTION

In a product aspect, the invention relates to 8-(4-fluorophenyl)-2,3,4,4a,5,6,11,11a-octahydro-11-a-methyl-4-(2-pyridinyl)-8H-phenanthro[2,3-c]pyrazole, having the formula:

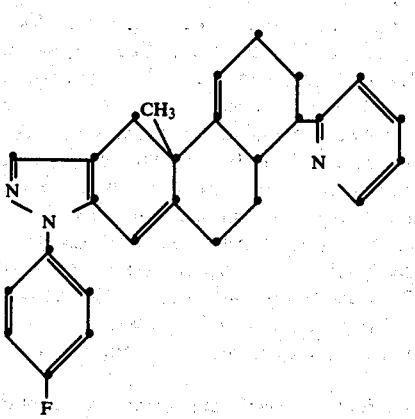

I

In a further product aspect, the invention relates to a pharmaceutical composition for treating inflammation in mammals which comprises an anti-inflammatorily effective amount of the compound of formula I and a pharmaceutically acceptable carrier.

In a process aspect, the invention relates to a process for preparing the compound of formula I by reacting 1-ethenyl-6-(4-fluorophenyl)-3,4,9,9a-tetrahydro-9a-methyl-6H-naphtho[2,3-c]pyrazole of the formula:

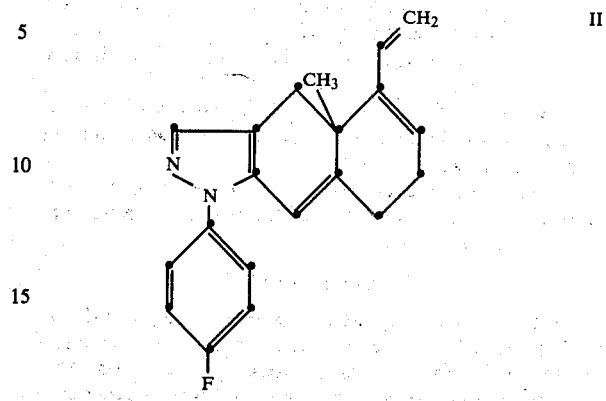

II with 2-vinylpyridine.

In a further process aspect, the invention relates to a method of reducing inflammation in a mammal which comprises administering to said mammal an anti-inflammatorily effective amount of the compound of formula I.

DETAILED DESCRIPTION INCLUSIVE OF PREFERRED EMBODIMENTS

The novel intermediate of formula II is prepared from a known starting material, 5-ethenyl-4,4a,7,8-tetrahydro-4a-methyl-2(3H)- naphthalenone (cf. Bell et al. U.S. Pat. No. 4,157,349, June 5, 1979) in accordance with the following reactions:

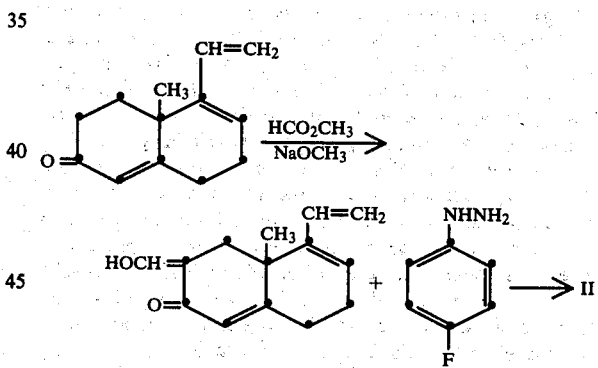

The trienone starting material is reacted with methyl formate in the presence of sodium methoxide in an inert solvent such as tetrahydrofuran to afford 5-ethenyl-3-hydroxymethylene-4,4a,7,8-tetrahydro-4a-methyl-2(3H)-naphthalenone, and the latter is then reacted with 4-fluorophenylhydrazine or an acid-addition salt thereof in the presence of acetic acid to give the compound of formula II.

The compound of formula I is prepared by reacting the compound of formula II with 2-vinylpyridine. The reaction takes place by heating the reactants in an inert solvent at a temperature between about 50° and 150° C. In order to suppress the tendency of the diene to polymerize, a small quantity of a free radical chain reaction inhibitor such as 1,2,3-benzenetriol (pyrogallol), may be added.

The compound of formula I exhibits an endocrinological profile characteristic of compounds possessing glucocorticoid properties and systemic and/or topical anti-inflammatory activity; cf. R. H. Silber, The Biology of Anti-inflammatory Steroids, Annals of the New York Academy of Sciences, Vol. 82, Art. 4, pp. 821–828.

When the compound of formula I is administered orally to rats it causes a significant depression in thymus weight, adrenal weight and body weight gain without a change in food consumption.

The compound of formula I has also been found to possess anti-inflammatory activity by the adjuvant arthritis test in rats.

The test procedures used to determine the biological activities of the compounds of the invention were carried out as follows:

Endocrine Profile

Mature female rats with an average body weight of 202 g and a body weight range of 15 g or less were medicated orally with test compound for 2 weeks. The test compound was prepared as a solution or suspension in 1% gum tragacanth or 0.75% methyl cellulose. On the day following the last medication, the rats were killed and the thymus and adrenal of each rat were removed, cleaned, and weighed. Body weights and food consumptions were also recorded.

Adjuvant Arthritis Test

Male rats (Charles River, Sprague Dawley strain) weighing 200–230 g were used. Adjuvant (*M. butyricum*, Difco Laboratories), 0.1 mL of a 0.6% suspension in heavy mineral oil, was injected into the plantar tissue of the left hind paw. The negative control group was injected with the mineral oil only. Beginning on the ninth day after adjuvant injection, the animals received 12 daily medications. The compound was suspended in 1% gum tragacanth and administered orally in a volume of 1 mL/100 g body weight. Both the negative control and adjuvant injected control groups received the gum tragacanth only. Twenty-four hours following the last medication, the animals were weighed and paw volumes were determined plethysmographically.

The compound of the invention can be formulated for topical application by solution or dispersion in a conventional pharmaceutically acceptable liquid, cream or ointment base. The effective ingredient is preferably present in a concentration of 0.01% to 5.0% by weight.

The compound of the invention can be formulated for oral administration in tablet or capsule form with conventional excipients. The active ingredient is preferably present in an amount of 1 mg to 100 mg per unit dosage form.

The following example will further illustrate the invention.

EXAMPLE (a)

5-Ethenyl-3-hydroxymethylene-4,4a,7,8-tetrahydro-4a-methyl-2(3H)-naphthalenone

A solution of 50.0 g (0.265 mol) of 5-ethenyl-4,4a,7,8-tetrahydro-4a-methyl-2(3H)-naphthalenone in 350 mL of tetrahydrofuran was cooled to −5° C. in an ice-methanol bath and stirred under nitrogen while 57.2 g (1.06 mol) of sodium methoxide was added. The resulting mixture was stirred for 30 min at −5° C. and then a solution of 114 mL (1.85 mol) of methyl formate in 100 mL of tetrahydrofuran was added slowly. The mixture was stirred overnight at room temperature and then poured onto a mixture of ice-water (1500 mL) and 6 N hydrochloric acid (265 mL). The product was extracted with ether and the combined extracts were washed with water. The dried extract was dried over anhydrous magnesium sulfate and concentrated in vacuo to afford an oil. This oil was triturated with hexane (4×250 mL) and the combined triturates were dried over magnesium sulfate and concentrated in vacuo to afford 55.37 g of a red oil, consisting essentially of the above-entitled compound as established by proton NMR (PMR) spectral data.

(b)

1-Ethenyl-6-(4-fluorophenyl)-3,4,9,9a-tetrahydro-9a-methyl-6H-naphtho[2,3-c]pyrazole (II)

4-Fluorophenylhydrazine hydrochloride (45.85 g, 0.282 mol) and sodium acetate (23.14 g, 0.282 mol) were added to a solution of 55.37 g (0.256 mol) of the product obtained in part (a) above in 225 mL of glacial acetic acid. The mixture was stirred overnight at room temperature and then concentrated in vacuo to afford a semi-solid. This material was suspended in ether (1 L) and filtered to remove sodium chloride. The ether filtrate was washed with water (4×250 mL), saturated sodium bicarbonate (until weakly basic) and saturated sodium chloride (100 mL). The extract was dried over anhydrous magnesium sulfate, decolorized with charcoal and concentrated in vacuo to afford an oil. This oil was triturated with 1:2 ether-hexane (3×750 mL) to afford 69.58 g of a dark brown oil. An analytical sample was prepared by using high-performance liquid chromatography with 1:3 ether-hexane as solvent. The resulting yellow oil was triturated with pentane to afford 1-ethenyl-6-(4-fluorophenyl)3,4,9,9a-tetrahydro-9a-methyl-6H-naphtho[2,3-c]pyrazole (II) as a yellow solid, m.p. 70°–72° C., with a consistent PMR spectrum.

(c)

8-(4-Fluorophenyl)-2,3,4,4a,5,6,11,11a-octahydro-11a-methyl-4-(2-pyridinyl)-8H-phenanthro[2,3-c]pyrazole (I)

A solution of 18.91 g (0.062 mol) of 1-ethenyl-6-(4-fluorophenyl)-3,4,9,9a-tetrahydro-9a-methyl-6H-naphtho[2,3-c]pyrazole (II), 7.33 mL (0.078 mol) of 2-vinylpyridine and 500 mg of 1,2,3-benzenetriol in 200 mL of xylene was refluxed for 60 hours. The reaction mixture was cooled and extracted with 2 N hydrochloric acid (4×100 mL). The combined extracts were filtered, made basic with 5 N sodium hydroxide and extracted with methylene dichloride (4×200 mL). The extract was dried over anhydrous sodium sulfate, decolorized with charcoal and concentrated in vacuo to afford a brown oil. The oil was triturated with ether to give a beige solid, 7.8 g, as a mixture of isomers of 8-(4-fluorophenyl)-2,3,4,4a,5,6,11,11a-octahydro-11a-methyl-4-(2-pyridinyl)-8H-phenanthro[2,3-c]pyrazole, m.p. 154°–156° C., as determined by proton NMR spectral data.

In the endocrine profile determination, Compound I at a dose level of 100 mg/kg caused a 64% reduction in thymus weight, 48% reduction in adrenal weight and 80% reduction in body weight loss as compared with the controls.

In the adjuvant arthritis test, compound I at a dose level of 133 mg/kg caused a 37% inhibition of the induced arthritis.

I claim:

1. 8-(4-Fluorophenyl)-2,3,4,4a,5,6,11,11a-octahydro-11a-methyl-4-(2-pyridinyl)-8H-phenanthro[2,3-c]pyrazole, having the formula

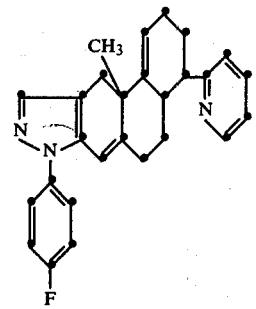

2. A pharmaceutical composition for treating inflammation in mammals which comprises an anti-inflammatorily effective amount of the compound according to claim 1 and a pharmaceutically acceptable carrier.

3. A method of reducing inflammation in a mammal which comprises administering to said mammal an anti-inflammatorily effective amount of the compound according to claim 1.

* * * * *